United States Patent [19]
Mathes

[11] 3,964,483
[45] June 22, 1976

[54] INHALATION DEVICE

[75] Inventor: Stanley Mathes, Mountain View, Calif.

[73] Assignee: Syntex Puerto Rico, Inc., Humacao, P.R.

[22] Filed: Jan. 13, 1975

[21] Appl. No.: 540,623

[52] U.S. Cl. .............................. 128/266; 128/206; 128/208
[51] Int. Cl.² ...................................... A61M 13/00
[58] Field of Search .................. 128/266, 206, 208; 222/193

[56] References Cited
UNITED STATES PATENTS

| | | | |
|---|---|---|---|
| 2,470,296 | 5/1949 | Fields | 128/206 |
| 2,517,482 | 8/1950 | Hall | 128/206 |
| 2,573,918 | 11/1951 | McCuiston | 128/206 |
| 3,807,400 | 4/1974 | Cocozza | 128/266 |
| 3,858,583 | 1/1975 | Hallworth | 128/266 |

Primary Examiner—Aldrich F. Medbery
Attorney, Agent, or Firm—Joseph I. Hirsch; William B. Walker

[57] ABSTRACT

An inhalation device having an elongate housing having one or more passageways for the passage of air therethrough. The passageway, of relatively small diameter, opens into an emptying chamber, of relatively greater diameter, adjacent that end of the housing which is adapted for insertion into the mouth or nose of a user. Adjacent that end of the emptying chamber closest to the passageway(s), the housing has means to hold a medicament-holding container so it is tilted toward the passageway (i.e., away from the output end of the housing). During inhalation, the powdered medicament in the container is entrained in the air stream being inhaled and is carried into the nose, throat, or lungs of the user where beneficial or therapeutic action of the medicament occurs.

16 Claims, 4 Drawing Figures

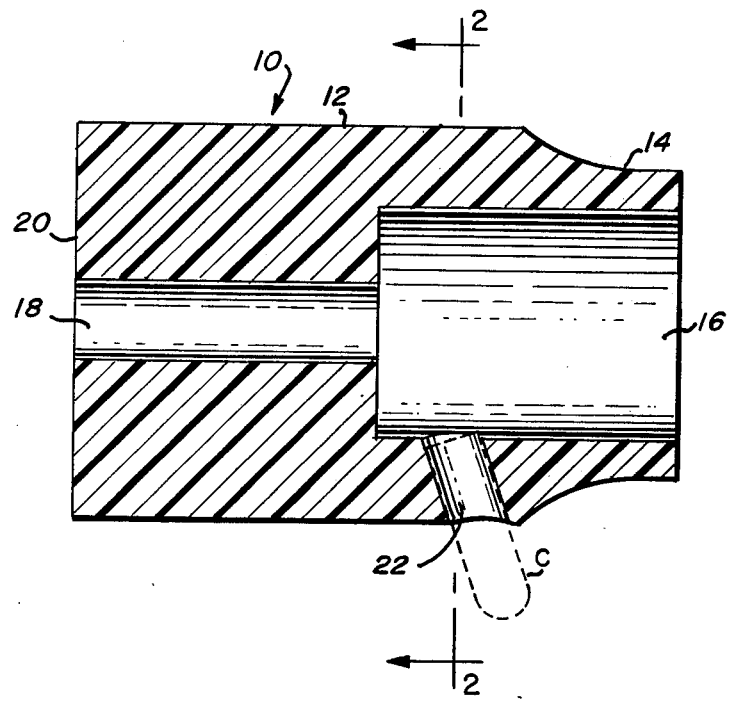
Fig_1
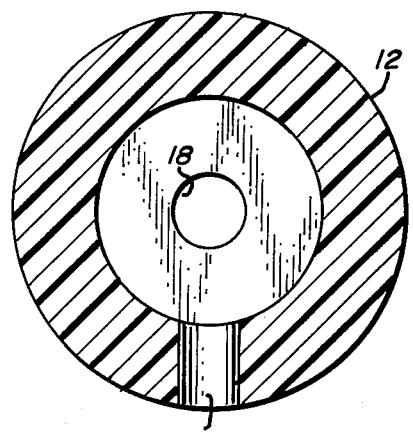
Fig_2

INHALATION DEVICE

FIELD OF THE INVENTION

This invention is related to devices for the administration of powdered medicaments by inhalation. More particularly, this invention relates to an inhalation device having, in the essential aspects thereof, no moving parts, yet which is capable of causing a powdered medicament, held within a container inserted into, or adjacent, the device, to be rapidly and effectively dispensed from the container, entrained in the air stream being inhaled and, thusly, carried into the nose, throat or lungs of the user where beneficial action of the medicament occurs.

BACKGROUND OF THE INVENTION

Known, prior art inhalation devices include, for example, those shown in U.S. Pat. Nos. 988,352; 2,507,702; and 2,603,281; and Great Britain Patent No. 1,118,431.

SUMMARY OF THE INVENTION

The inhalation devices of the present invention include an elongate housing having one or more passageways for the passage of air therethrough, one end of the housing being adapted for insertion into the mouth or nose of the user. The passageway(s) extending through the housing terminate in an emptying chamber adjacent the output end of the housing. Means are provided adjacent the intersection of the passageway(s) with the emptying chamber for presenting a unit dose of powdered medicament for administration by inhalation. As shown, the housing has a port or opening adapted to receive and hold a powdered medicament-holding container from which the medicament is to be entrained in the air stream passing through the device during inhalation. The port is tilted toward the passageway, that is, away from the output end of the housing. The axis of the port is at an angle of about 5° to about 40°, preferably about 10° to about 20°, from the vertical. Because of the orientation imparted to the medicament-holding container, a portion of the air stream passing through the device during inhalation causes the powder within the container to be expelled more readily, and then entrained in the air stream being inhaled and carried into the nose, throat or lungs of the user for beneficial action of the medicament to occur.

Container, as used herein, is intended to include any means by which a unit dose of medicament is presented to the device for administration. Capsules are the presently preferred form of containers; however, it is contemplated that other forms would be equally suitable if appropriate structural modifications to the device, to accommodate the different carrier, are made as, and if, necessary.

The container, in one aspect of the present invention, is manually opened, just prior to insertion into the device, to expose the medicament as is necessary for entrainment during inhalation. Optionally, in another aspect of this portion of the invention, the device can have a conventional means associated therewith for opening the container after it has been inserted into the device or for automatically opening the container as it is inserted into the device. In either case, such means eliminate the need to manually open the container prior to insertion, and, thusly, reduce the possibility of inadvertent spillage of the medicament prior to inhalation.

It has been found that, with the inhalation devices of this invention, the powdered medicament held within the container is rapidly and efficiently entrained in the air stream passing through the device during inhalation, and, as such, is carried into the nose, throat or lungs of the user where beneficial action of the medicament occurs.

BRIEF DESCRIPTION OF THE DRAWINGS

The foregoing and still further features and advantages of the present invention will become more apparent upon consideration of the following detailed description, taken together with the accompanying drawings wherein:

FIG. 1 is a vertical cross-sectional view of the inhalation device of the present invention;

FIG. 2 is a cross-sectional view of the inhalation device of FIG. 1 taken along line 2—2 of FIG. 1.

Figure 3:
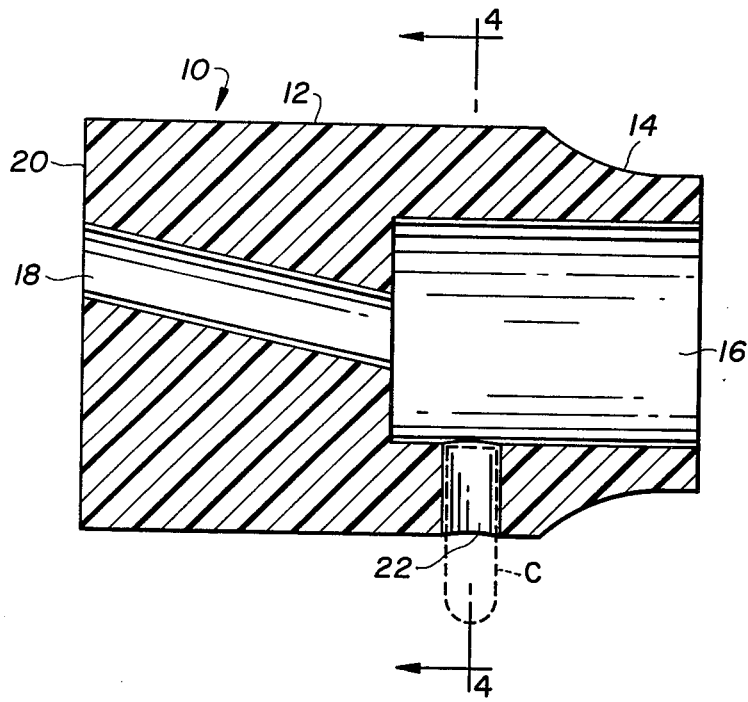
FIG. 3 is a vertical cross-sectional view of a further embodiment of the inhalation device of the present invention.

In the discussion below, reference will be made to a capsule as an exemplary container for presenting a medicament to the device for administration. As set forth above, other containers are contemplated for use with the device of this invention.

Referring to FIG. 1, there is shown an inhalation device 10 having a substantially cylindrical elongate housing 12 (as can best be seen in FIG. 2). At one end of housing 12 is a mouthpiece 14 intended for insertion into the mouth of a user thereof. Mouthpiece 14 can be redesigned to permit insertion into the nasal passages or, if desired, an adaptor (not shown) can be placed over the mouth piece to permit nasal use. Adjacent mouthpiece 14 is a cylindrical emptying chamber 16 connected at the inner end thereof to cylindrical passageway 18 which extends to the other end 20 of the device. If desired, passageway 18 can terminate in an incoming or entrance chamber of essentially similar or like configuration to emptying chamber 16. Adjacent the lower, inner end of chamber 16, there is an opening or port 22 into which an opened capsule C, as shown in dotted outline in FIG. 1, is inserted prior to inhalation. The manner of connecting passageway 18 with chamber 16 can be squared-off as shown or more streamlined, if desired, as long as the particular configuration selected is effective to cause the powdered medicament to be expelled from the capsule in the desired number of inhalations. During inhalation, the air stream passing along passageway 18 into emptying chamber 16 is effective to expel the powdered medicament from the capsule, and to have the expelled medicament entrained in the flowing air stream and carried into the throat or lungs of the user where beneficial action of the medicament occurs.

In use, the patient manually opens the medicament-holding capsule or other medicament-holding container and inserts the opened, medicament-holding portion thereof into port 22 essentially to the position shown in dotted outlines FIG. 1. The mouthpiece is inserted into the mouth and, upon inhalation, the air flowing through the device causes the medicament in the capsule to be entrained into the air stream flowing through emptying chamber 16.

As set forth above, well known means can be provided to automatically open the medicament-holding container upon insertion thereof into port 22, or means can be provided to open the medicament-holding container after it is inserted into the device. For example, a slide having a sharp cutting edge can be manually pushed across the top of the medicament-holding container, while held within the device, as within port 22, to slice open the top thereof and thereby expose the medicament to be administered. Or the capsule, as it is being inserted, can be caused to come into contact with a sharp cutting edge which also will slice open the top of the capsule and, thusly, expose the medicament to be administered. In either case, these means, and other means equivalent thereto, eliminate the need to manually open the container prior to insertion thereof into the inhalation device, thereby reducing the possibility of spillage of the medicament prior to inhalation.

The entire device can be made of metal but preferably is made of suitable plastic material, such as nylon, polyacetal or polypropylene and, as shown, is of unitary construction. This design enables the device to be manufactured quite readily, with substantial cost reduction in the manufacturing process, without adversely affecting medicament administration during inhalation.

The physical properties (i.e., flow characteristics) of each medicament formulation will affect the ease or manner in which it is dispensed with these or other inhalation devices. However, for a given powdered formulation, varying the diameter of passageway 18, the positioning of port 22 (from the position as shown toward the open end of chamber 16), the angle or tilt of port 22, and/or, in general, the overall configuration and shape of chamber 16 and passageway 18, the device of this invention can be designed to deliver the medicament in a different number of inhalations or in a longer or shorter period of time, depending upon the nasal or lung capacities of each particular user. Quite obviously, no single device will be suitable for all persons requiring administration of powdered medicaments since, for example, people with differing lung capacities are known to generate flow rates of about 30 liters/minute or so to about 120 liters/minute or so through inhalation devices of this and known types. Nonetheless, the device of this invention affords such variability, through proper selection of the various design parameters, that a device, embraced within the scope of this invention can be designed for a particular patient-generated flow rate to deliver the medicament according to a certain set of pre-determined objectives (for example, slow or fast administration, one or more inhalations, etc.). The net result is that a family of devices, all embraced within the present invention, can be designed, each of which will deliver the medicament under a given set of selected administration conditions. Conversely, the device of this invention can be designed to cover an extensive range of operating conditions, and thus be made suitable for use by a variety of persons having differing inhalation abilities or capacities.

Figure 4:
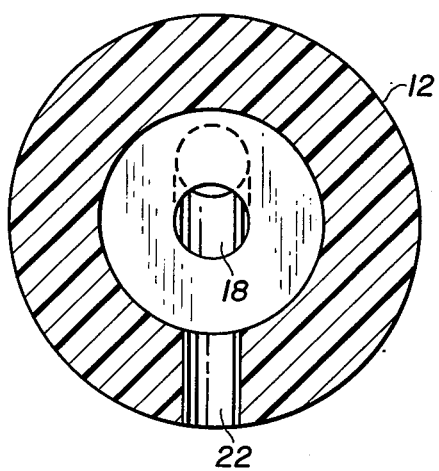
FIG. 4 is a cross-sectional view of the inhalation device of FIG. 3 taken along line 4—4 of FIG. 3.

While the present invention has been described with reference to specific embodiments thereof, it will be understood by those skilled in this art that various changes may be made and equivalents may be substituted without departing from the true spirit and scope of the invention. For example, port 22 can be vertically positioned and passageway 18 can be angled downwardly with respect to the longitudinal axis of the housing. This embodiment of the present invention is shown in FIGS. 3 and 4 where like numerals are utilized to the corresponding elements of the inhalation device of FIGS. 1 and 2. Additionally, other modifications may be made to adapt a particular situation, material or composition of matter, structural desirability, or then-present objective to the spirit of this invention without departing from its essential teachings.

What is claimed is:

1. An inhalation device for dispensing a medicament from a medicament-holding container comprising an elongate housing having a passageway for the movement of air therethrough, one end of said housing being an output end adapted for insertion into the mouth or nasal passages of a user thereof; said passageway terminating in an emptying chamber located adjacent the output end of said housing, the cross-sectional area of said passage-way being less than the cross sectional area of said emptying chamber; and means extending through a side wall of said housing from the outside and opening into said emptying chamber for receiving a medicament-holding container, said container receiving means being tilted at an angle toward said passageway, whereby, during inhalation, a component of the air flowing through said passageway flows into the container receiving means whereby the medicament held in a medicament-holding container is dispensed therefrom.

2. The device of claim 1 wherein said container holding means comprises an opening in said housing tilted toward said passageway.

3. The device of claim 1 wherein said container holding means comprises an opening in said housing tilted toward said passageway at an angle of about 5° to about 40° from the vertical.

4. The device of claim 3 wherein said opening is tilted toward said passageway at an angle of about 10° to about 20° from the vertical.

5. The device of claim 1 wherein said container receiving means is closely adjacent the interface between said passageway and said emptying chamber.

6. The device of claim 1 wherein said emptying chamber and said passageway are substantially cylindrical.

7. An inhalation device for dispensing a medicament from a medicament-holding container comprising an elongate housing having a passageway for the movement of air therethrough, one end of said housing being an output end adapted for insertion into the mouth or nasal passages of a user thereof, said passageway terminating in an emptying chamber located adjacent the output end of said housing, the cross-sectional area of said passageway being less than the cross-sectional area of said emptying chamber; a port extending through a side wall of said housing from the outside adjacent the interface between said passageway and said emptying chamber and opening into said emptying chamber for receiving a medicament-holding container, said port being tilted toward said passageway at an angle of about 5° to about 40° from the vertical whereby, during inhalation, a component of the air flowing through said passageway flows into the container receiving means whereby the medicament held within a medicament-holding container is dispensed therefrom.

8. The device of claim 7 wherein said opening is tilted toward said passageway at an angle of about 10° to about 20° from the vertical.

9. The device of claim 7 wherein said emptying chamber and said passageway are substantially cylindrical.

10. An inhalation device for dispensing a medicament-holding container comprising an elongate housing having a passageway for the movement of air therethrough, one end of said housing being an output end adapted for insertion into the mouth or nasal passages of a user thereof; said passageway terminating in an emptying chamber located adjacent the output end of said housing, the cross-sectional area of said passageway being less than the cross-sectional area of said emptying chamber; and means extending through a side wall of said housing from the outside and opening into said emptying chamber adjacent the passageway for receiving a medicament-holding container, said container receiving means being at an angle relative to the direction of air flow as it exits from said passageway, whereby, during inhalation, a component of the air flowing through said passageway flows into the container receiving means whereby the medicament held in a medicament-holding container is dispensed therefrom.

11. The device of claim 10 wherein said container receiving means comprises an opening in said housing, the axis of said opening being substantially perpendicular to the longitudinal axis of said housing, said passageway being angled with respect to the longitudinal axis of said housing.

12. The device of claim 11 wherein said passageway is substantially cylindrical having a straight longitudinal axis.

13. The device of claim 1 wherein said passageway extends longitudinally through said housing.

14. The device of claim 1 wherein said container receiving means is intermediate the output end of said housing and the interface of said passageway with said emptying chamber.

15. The device of claim 7 wherein said passageway extends longitudinally through said housing.

16. The device of claim 7 wherein said port is intermediate the output end of said housing and the interface of said passageway with said emptying chamber.

* * * * *